United States Patent [19]
Reznik

[11] Patent Number: 6,030,816
[45] Date of Patent: Feb. 29, 2000

[54] HEATING AND PROCESSING STARCH SOLUTIONS

[76] Inventor: David Reznik, 12690 Viscaino Rd., Los Altos Hills, Calif. 94022

[21] Appl. No.: 09/360,924

[22] Filed: Jul. 26, 1999

[51] Int. Cl.[7] .............................. C12P 19/14; C13K 1/06
[52] U.S. Cl. ................................ 435/99; 127/38
[58] Field of Search ................. 435/99; 127/38

[56] References Cited

U.S. PATENT DOCUMENTS 4,014,743  3/1977  Black ...................... 195/31 R
4,235,965  11/1980  Walon ......................... 435/95

Primary Examiner—David Brunsman
Attorney, Agent, or Firm—Darby & Darby

[57] ABSTRACT

A method for heating starch solutions, including heating a dilute starch-water slurry, preferably containing about 8–12% starch, to a temperature of about 100–115° C., adding starch to the dilute slurry, and dextrinating the starch in the slurry to reach a final slurry of 35–40% solid content, the solid content including at least one of dextrins and soluble broken starch chains.

11 Claims, 1 Drawing Sheet

HEATING AND PROCESSING STARCH SOLUTIONS

FIELD OF THE INVENTION

The present invention relates to generally to methods and apparatus for heating starch solutions and particularly to heating starch slurry solutions and processing them into dextrin, all the while preventing significant gelation of the slurry so as to maintain efficient pumpability of the slurry.

BACKGROUND OF THE INVENTION

In certain food industries, such as in the production of glucose, corn syrup, and the like from starch, starch slurry must be converted by means of enzymes into dextrins and then into glucose. In general, industry-standard starch slurry consists of about 65% water and 35% starch. In high speed, high volume production lines, this slurry is pumped from one station to another during processing thereof The ideal temperature for a widely-used enzyme, alpha amylase, to hydrolyze the starch into dextrins is about 100–115° C. Unfortunately, a 35% starch slurry starts to gel at about 70° C., and its viscosity remains high until most of the starch has been hydrolyzed at about 102° C. This causes significant increases in the cost and power required to pump the gelatinous and viscous fluid from one station to another in the production line. Rapid heating of the slurry to 102° C. in an effort to "bypass" the high viscosity phase does not solve the problem because the breakdown of the starch is relatively slow, with the result that the fluid remains viscous.

SUMMARY OF THE INVENTION

The present invention seeks to provide improved methods and apparatus for heating starch slurry solutions and processing them into dextrin, all the while preventing significant gelation of the slurry so as to maintain efficient pumpability of the slurry.

The basic principle of the present invention is to initially heat a dihile solution of starch slurry, preferably about 8–12% starch content, rather than the industry-standard initial 35% starch content. This dilute solution does not gel at 70° C. nor at 102° C., and is fully pumpable, i.e., does not have a significantly higher viscosity and thus does not significantly increase pumping power and costs. In one aspect of the invention, a batch process, the dilute starch slurry is heated to about 102° C., all the time remaining pumpable, and concentrated slurry is intermittently and gradually added to reach a final slurry of 35–40% solid content (in the form of soluble broken starch chains or dextrins) for further processing, such as into glucose.

In another aspect of the invention, a production line process, the 8–12% starch-content slurry is dextrinated and more 8–12% starch is added, preferably in the form of concentrated slurry or dry starch, and allowed to dextrinate. The starch is gradually added to the pumped fluid along a production line until the total solids (in the form of dextrins and/or soluble broken starch chains) reach a concentration of about 35–40%. The fluid is fully pumpable at all times. It is noted that with the methods and apparatus of the present invention, a 40% or greater total solid content can also be achieved.

There is thus provided in accordance with a preferred embodiment of the present invention a method for heating starch solutions, including heating a dilute starch-water slurry, preferably containing about 8–12% starch, to a temperature of about 100–115° C., adding starch to the dilute slurry, and dextrinating the starch in the slurry to reach a final slurry of 35–40% solid content.

In accordance with a preferred embodiment of the present invention the final slurry is processed into glucose or other products.

Further in accordance with a preferred embodiment of the present invention the dilute starch-water slurry is pumped before reaching the final slurry of 35–40% solid content.

There is also provided in accordance with a preferred embodiment of the present invention a method for heating starch solutions, including (a) heating a dilute starch-water slurry, preferably containing about 8–12% starch, to a temperature of about 100–115° C., (b) dextrinating the dilute slurry to form an intermediate slurry with a solid content, the solid content including at least one of dextrins and soluble broken starch chains, (c) adding about starch to the intermediate slurry to form an 8–12% starch slurry, and (d) dextrinating the starch slurry.

In accordance with a preferred embodiment of the present invention steps (c) and (d) are repeated until obtaining a final slurry of about 35–40% solid content.

Further in accordance with a preferred embodiment of the present invention step (c) includes adding powdered starch, concentrated starch slurry or hot gelled (such as 50% starch slurry) to the intermediate slurry, preferably at a temperature of about 100–115° C.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
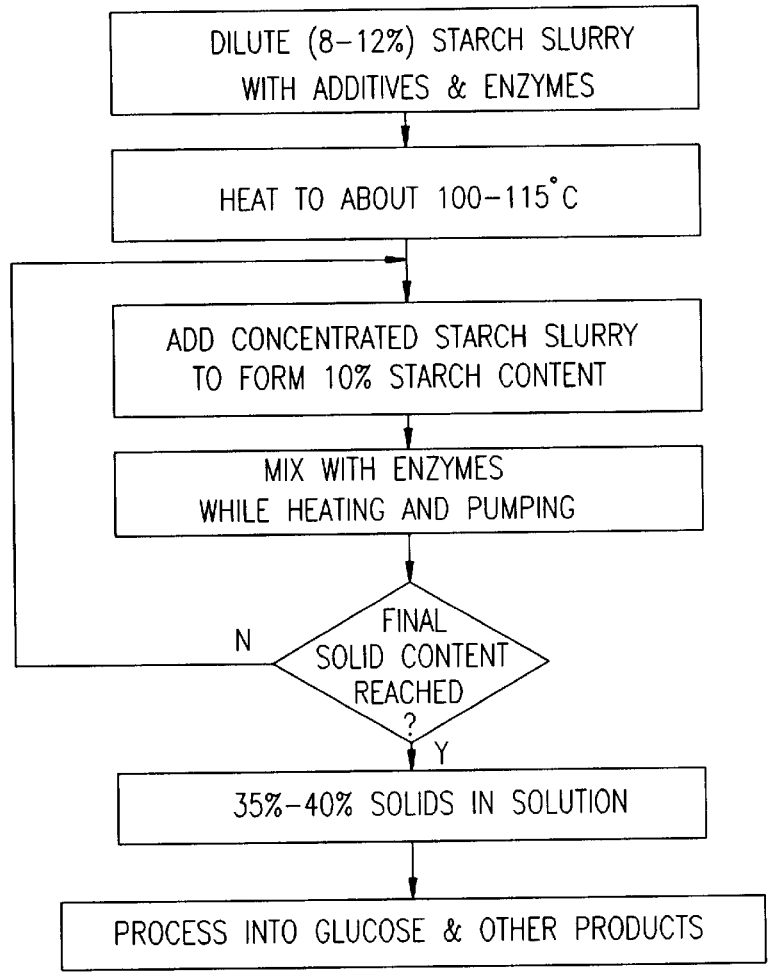
FIG. 1 is a simplified flow chart of a method and apparatus for heating and pumping starch slurry, constructed and operative in accordance with a preferred embodiment of the present invention.

Reference is now made to FIG. 1 which illustrates a method and apparatus for heating and pumping starch slurry in accordance with a preferred embodiment of the present invention.

A dilute solution of starch slurry, about 8–12% starch content, is heated to about 100–115° C. in the presence of enzymes to hydrolyze the starch into dextrins. The viscosity of the heated dilute solution does not significantly increase, meaning that the solution is readily pumpable by conventional and relatively inexpensive means. Starch is added to the solution to bring the insoluble starch content of the fluid back to about 8–12%. The starch may be added as a concentrated starch slurry. The starch contained in the solution is once again hydrolyzed with enzymes, thereby increasing the solid content (in the form of dextrins and/or soluble broken starch chains) of the fluid.

The process repeats itself until a desired final solid content is reached, such as 35–40% solid content (in the form of dextrins and/or soluble broken starch chains). In this manner the high viscosity phase of 35% starch-content slurry is avoided and the abovementioned pumping problem of the prior art is solved. At any point of the process, the starch content does not exceed 10%, although the solid content increases.

It is noted that dilute solutions other than 8–12% may also be pumpable, although the inventor has found that even 17% starch-content slurry gels at 7° C.

The starch slurry may be heated by any known means. A particularly efficient and advantageous method of heating the slurry is by means of ohmic heating, such as the rapid heating methods disclosed in applicant/assignee's U.S. Pat. Nos. 4,739,140; 5,583,960; 5,636,317 and 5,863,580, the disclosures of which are incorporated herein by reference.

Figure 2:
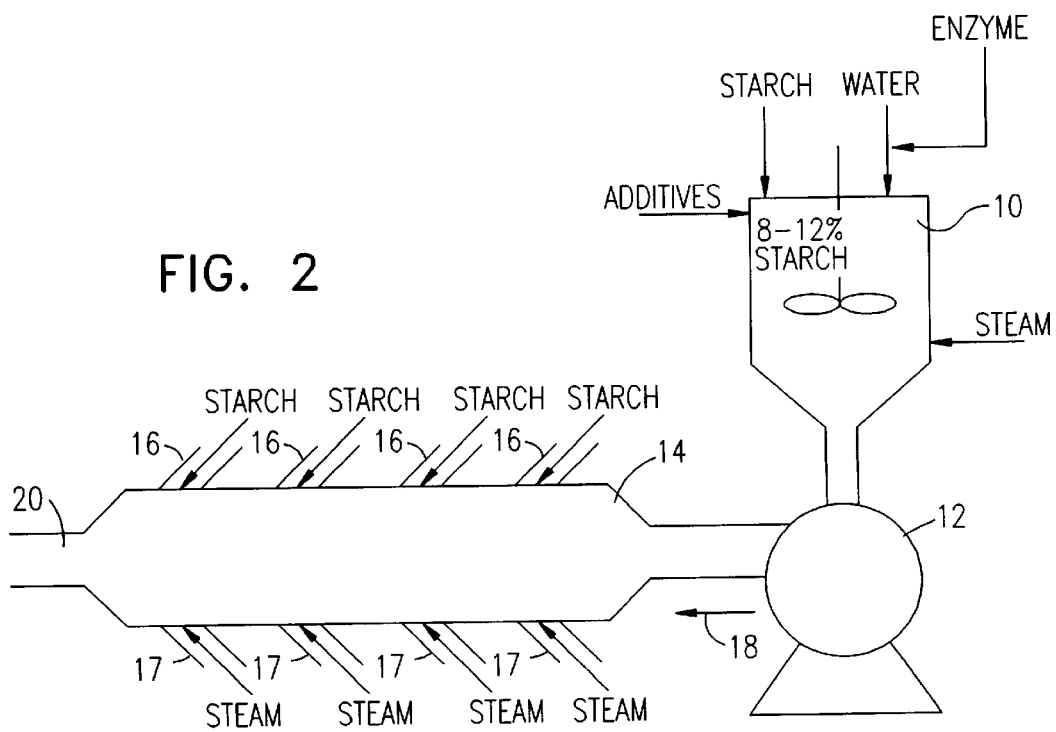
FIG. 2 is a simplified block diagram illustration of a method and apparatus for heating and pumping starch slurry, constructed and operative in accordance with another preferred embodiment of the present invention.

Reference is now made to FIG. 2 which illustrates a method and apparatus for heating and pumping starch slurry in accordance with another preferred embodiment of the present invention (production line).

Starch slurry is introduced into a mixing chamber 10 and heated (or pre-heated before entering the chamber 10) to about 102° C., such as by steam injection or any other convenient means. Additives may be added to the aqueous starch slurry, such as calcium or pH correction additives, for example. An enzyme, typically alpha amylase, is preferably added in an amount as required for the particular processing procedure. Starch is then introduced in an amount such that the starch is about 8–12% of the aqueous mixture.

The starch mixture is processed for an adequate time to complete dextrination (typically in the order of a few seconds). Chamber 10 is preferably heated and maintained at an optimum temperature for the enzyme to hydrolyze the starch into dextrin, typically 102° C., by means of a steam jacket, steam injection or ohmic heating, for example. In the illustrated embodiment, steam is introduced through inlets 17 along elongate chamber 14.

Starch, such as in the form of concentrated starch slurry, hot gelled slurry or powdered starch, is then added to the fluid in chamber 10 so as not to exceed a concentration of about 8–12% raw starch in the fluid. The inventor has found that 8–12% starch in the fluid does not gel in the temperature range of 70–102° C. and is fully pumpable, i.e., it does not significantly increase the viscosity of the starch-less fluid and thus does not significantly increase pumping power and costs.

A pump 12 pumps the 8–12% starch-containing fluid to an elongate chamber 14, wherein the starch contained in the fluid is dextrinated by the enzyme. Elongate chamber 14 has one or more inlets 16 for adding therethrough starch and additives as required. As the fluid is pumped through elongate chamber 14 generally in the direction of an arrow 18, starch, such as in the form of concentrated starch slurry, hot gelled slurry (preferably up to 50% starch) or most preferably powdered starch, is then added to the fluid, preferably in an amount such that at each inlet 16 a quantity of about 8–12% starch is further added to the fluid which is then dextrinated. Powdered starch can be added in any convenient and known manner, such as by means of readily commercially available equipment used for mixing milk powder in water or milk. Powder may be typically injected through a vortex or low pressure formed by a venturi effect of flowing fluid. An advantage in adding powdered starch is that no heat generally needs to be added during mixing of the fluid, especially if elongate chamber 14 is well insulated and the dextrination process is quick. Also water is not added, thus decreasing the size of chamber 14.

It is noted that by adding the starch in the form of hot gelled slurry (pre-heated to the processing temperature of 100–115° C.) can be advantageous in that it may obviate the need for heating elongate chamber 14. The gelled 50% starch slurry can be introduced in a manner similar to that used for the starch powder.

The soluble starch concentration is gradually increased along elongate chamber 14, the fluid remaining fully pumpable at all times and stations. At an exit 20 of elongate chamber 14, the final dextrin-containing fluid has a solid content of 35–40% (in the form of dextrins and/or soluble broken starch chains). It is noted that with the methods and apparatus of the present invention, a 40% or greater solid content can also be achieved.

It will be appreciated by persons skilled in the art that the present invention is not limited to what has been particularly shown and described hereinabove. Rather, the scope of the present invention is defined only by the claims that follow:

What is claimed is:

1. A method for heating starch solutions, comprising:
   heating a dilute starch-water slurry to a temperature of about 100–115° C.;
   adding starch to said dilute slurry; and
   dextrinating said starch in said slurry to reach a final slurry of 35–40% solid content.

2. The method according to claim 1 wherein said dilute starch-water slurry contains about 8–12% starch.

3. The method according to claim 1 further comprising processing the final slurry into glucose.

4. The method according to claim 1 further comprising pumping the dilute starch-water slurry before reaching the final slurry of 35–40% solid content.

5. A method for heating starch solutions, comprising:
   (a) heating a dilute starch-water slurry to a temperature of about 100–115° C.;
   (b) dextrinating the dilute slurry to form an intermediate slurry with a solid content, said solid content comprising at least one of dextrins and soluble broken starch chains;
   (c) adding about 8–12% starch to the intermediate slurry; and
   (d) dextrinating the intermediate slurry.

6. The method according to claim 5 wherein said dilute starch-water slurry in step (a) contains about 8–12% starch.

7. The method according to claim 5 further comprising repeating steps (c) and (d) until obtaining a final slurry of about 35–40% solid content.

8. The method according to claim 5 wherein step (c) comprises adding powdered starch to the intermediate slurry.

9. The method according to claim 5 wherein step (c) comprises adding concentrated starch slurry to the intermediate slurry.

10. The method according to claim 5 wherein step (c) comprises adding the starch in a hot gelled form to the intermediate slurry.

11. The method according to claim 5 wherein step (c) is carried out at a temperature of about 100–115° C.

* * * * *